United States Patent
Mlungwana

(10) Patent No.: US 12,329,533 B2
(45) Date of Patent: Jun. 17, 2025

(54) BALANCE TEST DEVICE AND SYSTEM FOR A MODERN FUNCTIONAL REACH TEST KIT

(71) Applicant: Dumisani Mlungwana, Yorktown, IN (US)

(72) Inventor: Dumisani Mlungwana, Yorktown, IN (US)

( * ) Notice: Subject to any disclaimer, the term of this patent is extended or adjusted under 35 U.S.C. 154(b) by 763 days.

(21) Appl. No.: 17/396,619

(22) Filed: Aug. 6, 2021

(65) Prior Publication Data
US 2022/0039731 A1    Feb. 10, 2022

Related U.S. Application Data

(60) Provisional application No. 63/062,594, filed on Aug. 7, 2020.

(51) Int. Cl.
*A61B 5/00*    (2006.01)

(52) U.S. Cl.
CPC .... *A61B 5/4023* (2013.01); *A61B 2560/0223* (2013.01); *A61B 2560/0431* (2013.01)

(58) Field of Classification Search
CPC ............ A61B 5/4023; A61B 2017/603; A47B 2220/11; F16M 13/08
USPC .......................................................... 600/300
See application file for complete search history.

(56) References Cited

U.S. PATENT DOCUMENTS

| | | | |
|---|---|---|---|
| 7,972,246 B2 | 7/2011 | Shinomiya et al. | |
| 10,856,629 B1 * | 12/2020 | Unice | A45B 1/00 |
| 2005/0207749 A1 * | 9/2005 | Barker | F16M 11/28 |
| | | | 396/428 |
| 2006/0073941 A1 | 4/2006 | Perry et al. | |
| 2006/0251334 A1 | 12/2006 | Oba et al. | |
| 2008/0281550 A1 | 12/2008 | Hogle et al. | |
| 2009/0299233 A1 * | 12/2009 | Wang | A61B 5/4023 |
| | | | 600/595 |
| 2012/0101411 A1 | 4/2012 | Hausdorff et al. | |
| 2015/0116120 A1 | 4/2015 | Watanabe | |

* cited by examiner

*Primary Examiner* — Nadia A Mahmood
(74) *Attorney, Agent, or Firm* — Ritchison Law Offices, PC; John Ritchison

(57) ABSTRACT

This is a Balance Test device and system for a Modern Functional Reach Test Kit as a system and method for characterizing balance function. The major characteristics are lightweight, compact, durable, lightweight, portable, and rigid. The Balance Test is a non-invasive measuring device used to perform a functional reach test to assess balance and functional motion to help determine if patients are ready to be released from hospital settings.

5 Claims, 12 Drawing Sheets

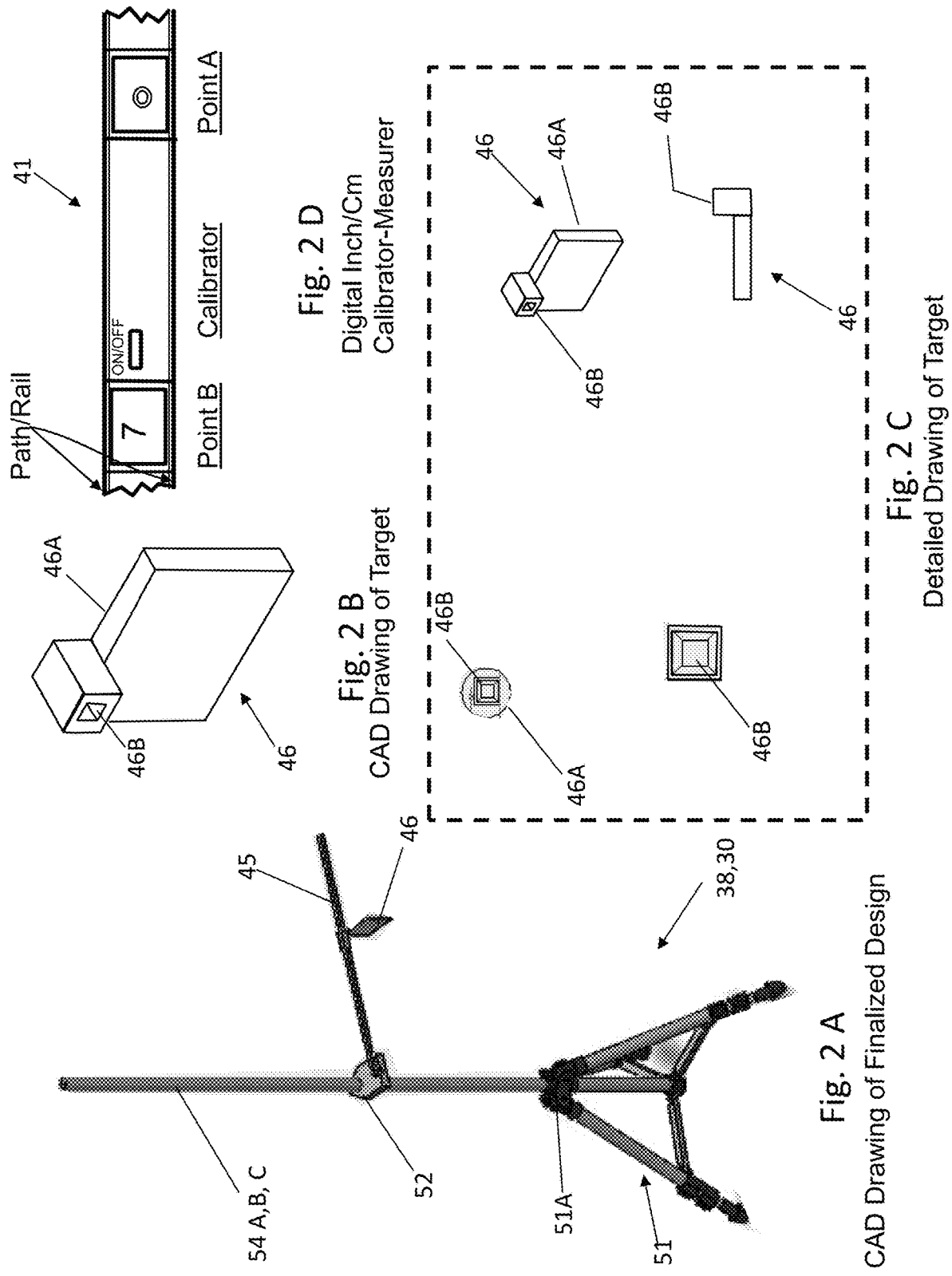

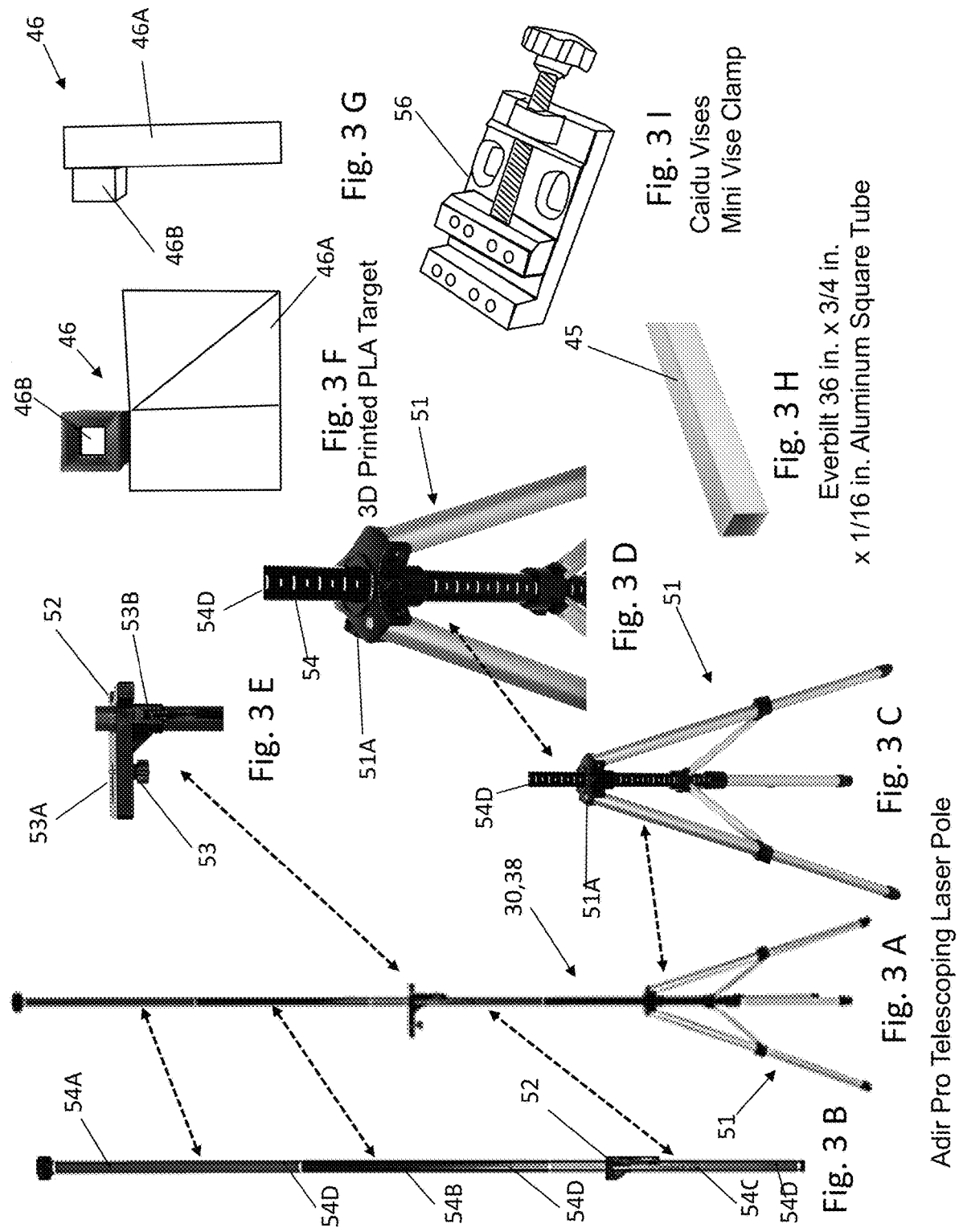

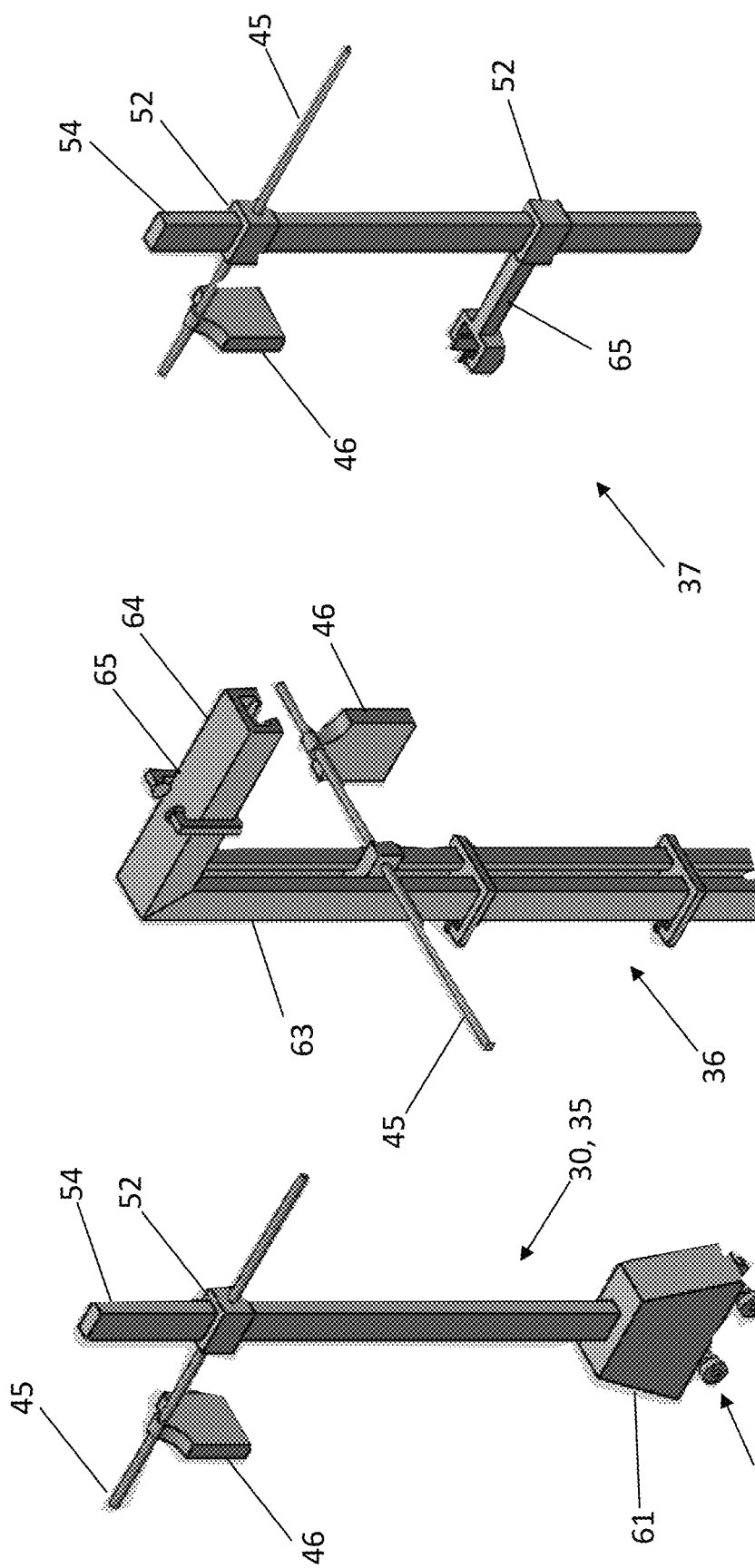

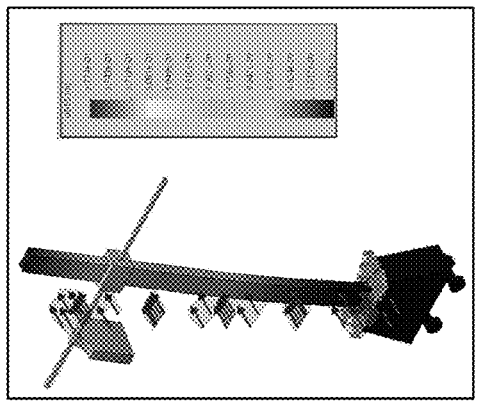
Fig. 5 A
Stress plot of Prototype 1-35
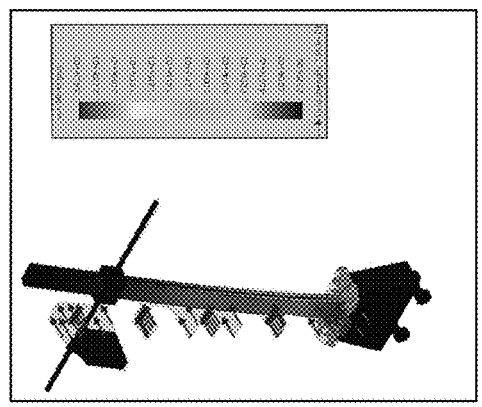
Fig. 5 B
Displacement plot of prototype 1 - 35
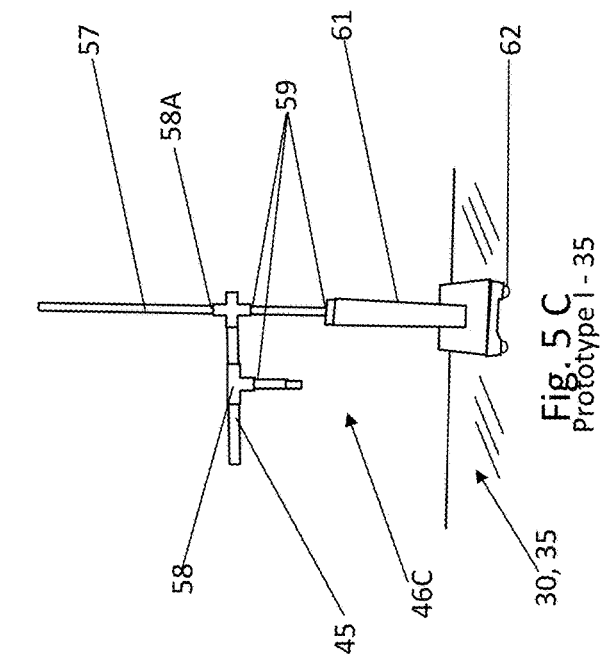
Fig. 5 C
Prototype I - 35
Fig. 5 D
Prototype II - 38

Figure 6:
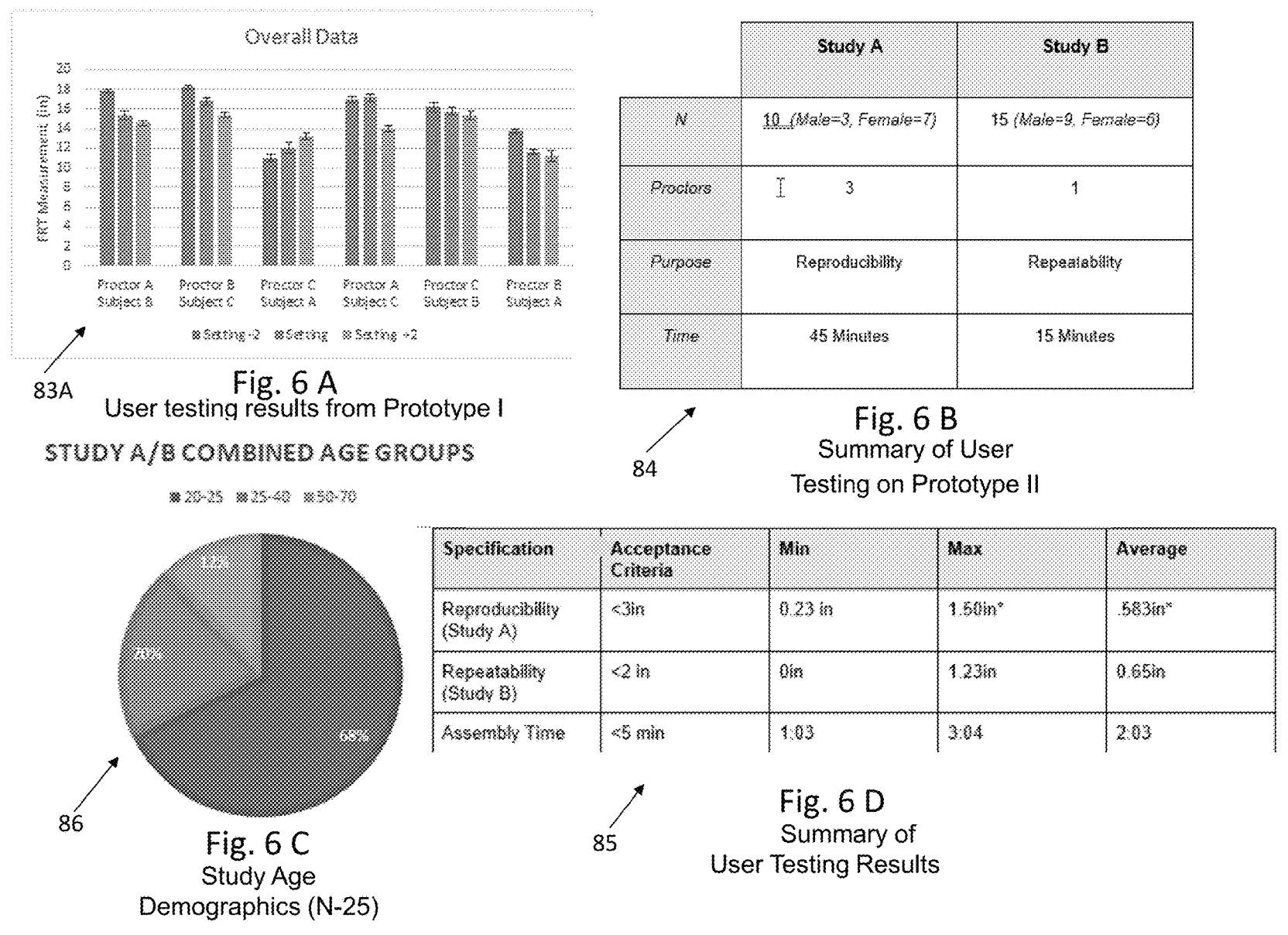

Fig. 6 A User testing results from Prototype I
STUDY A/B COMBINED AGE GROUPS

Fig. 6 B Summary of User Testing on Prototype II

Fig. 6 C Study Age Demographics (N-25)

Fig. 6 D Summary of User Testing Results

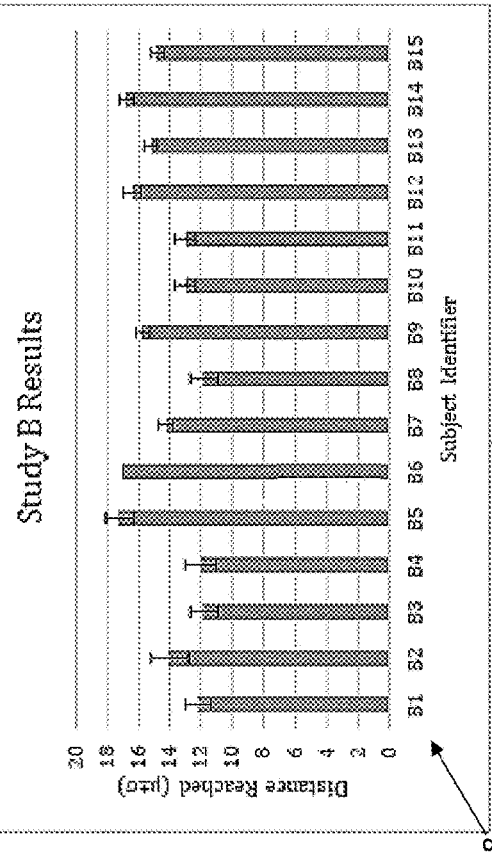
Fig. 7 A  Results from reproducibility study (N = 10) with college-aged male and female students.
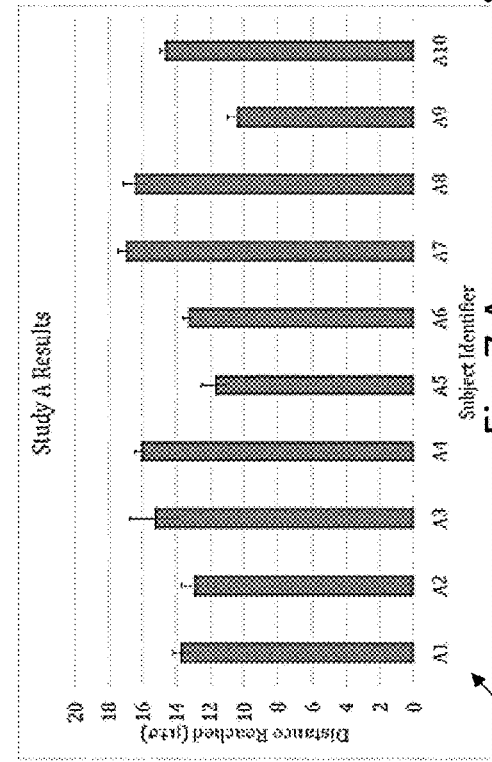
Fig. 7 B  Results from repeatability study (N = 15) with subjects ages 40 (N = 5), 50-70 (N = 3)
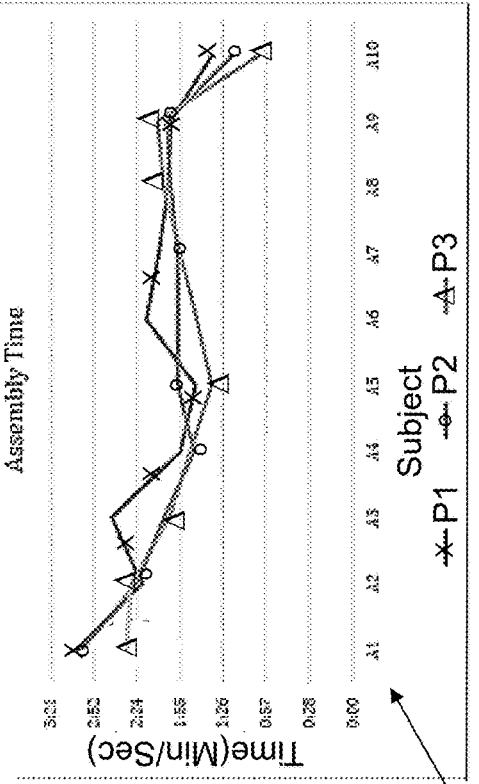
Fig. 7 C  Assembly time progression from Study A divided by proctor number.

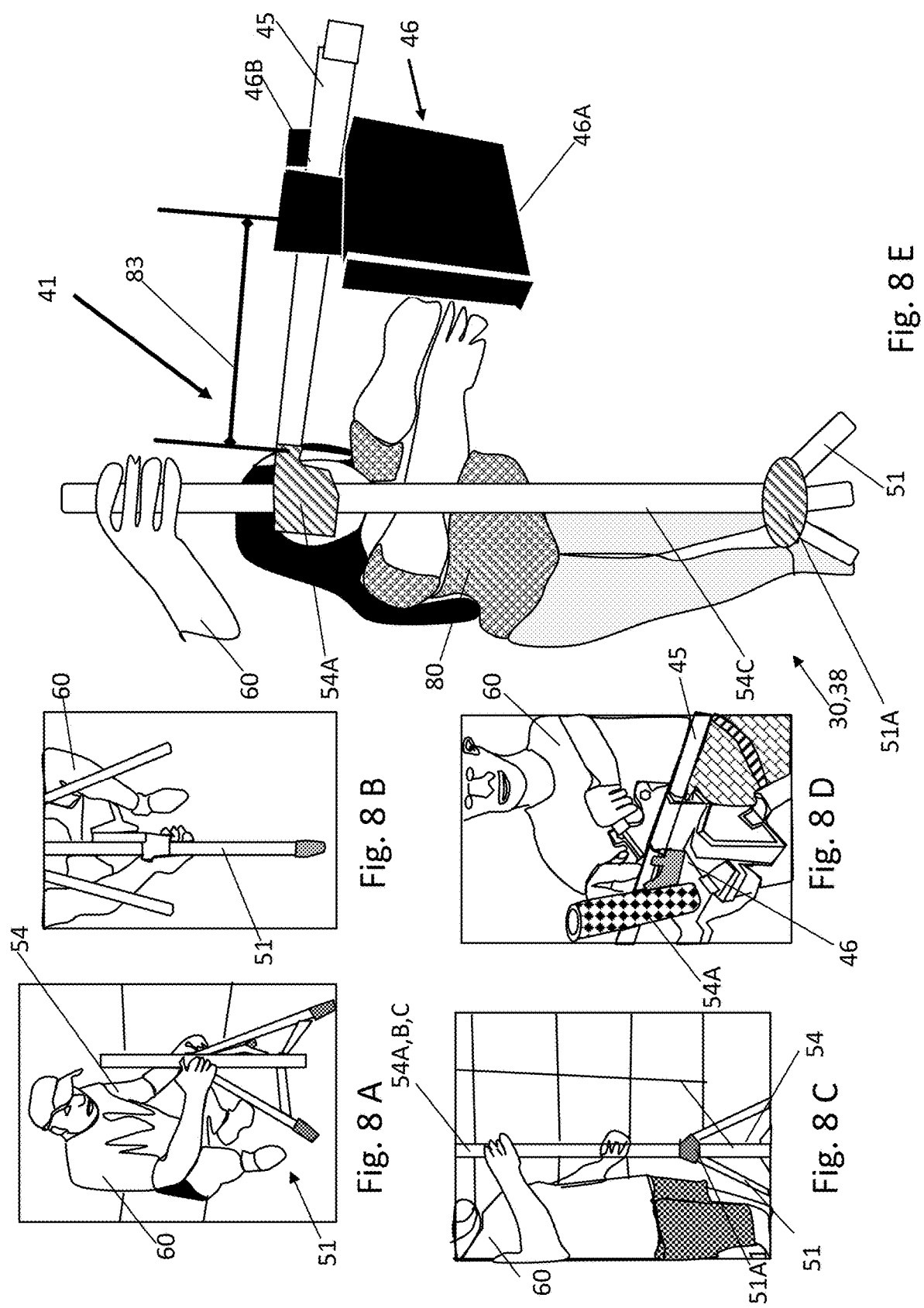

Instructional pamphlet, View A

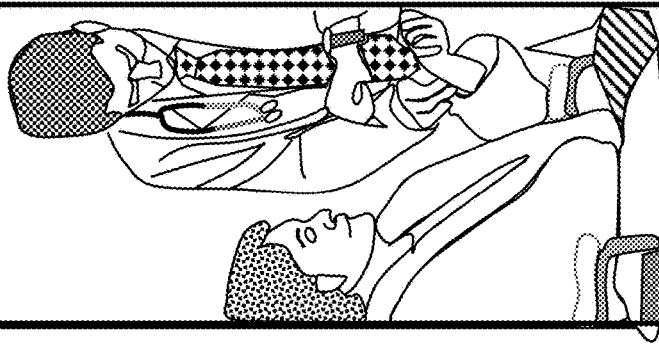

| Purpose: | Setting it up: |
|---|---|
| The Fundamental Reach Test is a non-invasive measuring device used to perform a functional reach test to assess balance and functional motion to help determine if patients are ready to be released from hospital settings. The Functional Reach Test Kit is easy to use, portable and more consistent than the current method.<br><br>It is intended to use at the practitioners discretion for the qualification of balance and mobility by providing a comprehensive system that produces reliable measurements taking into account posture and orientation while preventing overextension. | 1. Layout all of the components and open up the tripod legs.<br>2. Insert the top of pole 1 through the bottom and top rings of the tripod and set in place with the set screw located on the top ring of the tripod.<br>3. Expand the tripod legs and put the device on the ground so it is in a level position.<br>4. Screw in pole 2 to the top of pole 1.<br>5. Slide the platform with the vise on top over pole 2 and back into position using the cam lever.<br>6. Slide the target onto the horizontal calibrator as shown in the figure to the right.<br>7. Attach the horizontal calibrator using the vice. Make sure the ruler side of the horizontal bar is facing towards the pole and the position where the slider will start is able to reach the zero position. |

Figure 9A:
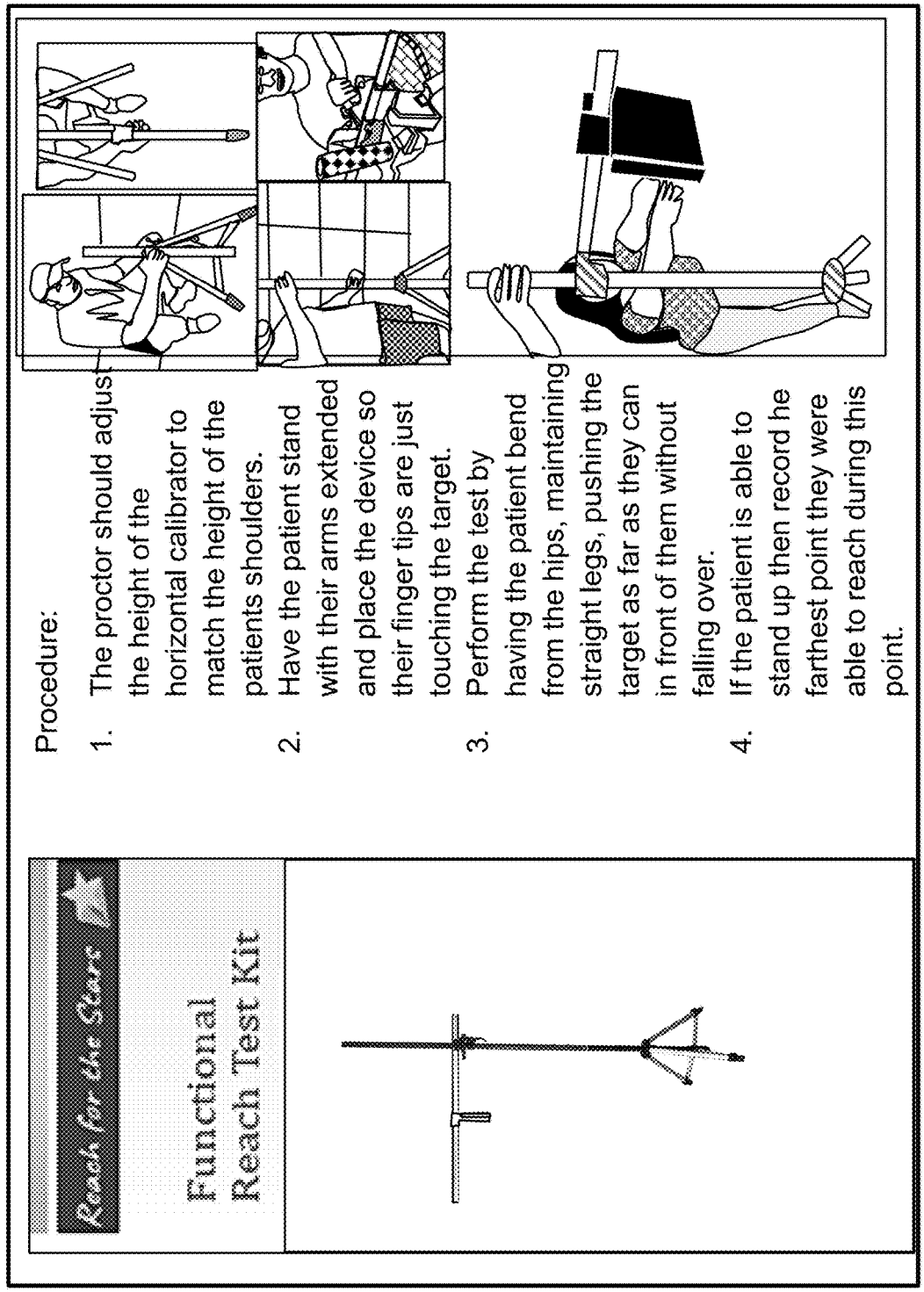

Fig. 9 B
Instructional pamphlet, View B

US Patent Appn.
US2015/0116120

US Patent Appn.
20060251334

US Patent Appn. US2006/0073941

US Patent Appn. US2006/0251334

US Patent 7,972,246

BALANCE TEST DEVICE AND SYSTEM FOR A MODERN FUNCTIONAL REACH TEST KIT

CROSS-REFERENCE TO RELATED APPLICATIONS

This application claims the benefit of U.S. Provisional Patent Application with Ser. No. 63/062,594 filed Aug. 7, 2020, by Dumisani Mlungwana. The application is entitled "Balance Test device and system for a Modern Functional Reach Test Kit".

FIELD OF INVENTION

This invention relates to a Balance Test device and system for a Modern Functional Reach Test Kit. The present invention relates to systems and methods for characterizing balance function. In particular, the present invention provides systems and methods for monitoring balance function. Systems and methods of the present invention find use in, among other things, research, diagnostic and therapeutic applications. The present invention, in some embodiments thereof, relates to motion detection, and more particularly, but not exclusively, to a system useful for identifying balance and reach related to motion.

FEDERALLY SPONSORED RESEARCH

None.

SEQUENCE LISTING OR PROGRAM

None.

BACKGROUND

Field of Invention and Prior Art

This section is not Applicable to Provisional Applications. However, as far as known, there are no Balance Test device and system for a Modern Functional Reach Test Kit or the like. It is believed that this product is unique in its design and technologies. The functional reach test (FRT) is used as an assessment of balance and mobility used as an indicator of fall risk. This is often used in patients with compromised mobility, such as those suffering from a stroke or movement disorder. The test is used as a condition of hospital release. Current FRT methods lack in portability and accuracy; we are creating a device that will address these issues.

Background

A public health issue of concern is the incidence of falls, in which a person falls to the ground from an upright position while standing or walking the problem of falls affects the elderly in general and is of particular concern for older persons and others who have a movement disorder or other illness that affects balance and motor control, such as Parkinson's disease. The effect of a fall on an elderly person can be particularly serious since many elderly people have weak or brittle bones and are generally further weakened by other illnesses and the effects of aging. In some cases, a fall causes the death of a person, either at the time of the fall or indirectly because of the injuries sustained. The type of injuries commonly experienced may include one or more of: a broken or fractured hip and other bones, head injuries, internal and external bleeding, and soft tissue and skin damage. The patient will most likely suffer a great deal of pain and may require hospitalization. In addition, he or she may face the prospect of long term or permanent loss of mobility, since their age and condition may mean that the injuries will take a long time to heal or may never heal completely. The patient may be plagued by fear of a recurrence, so that their mobility and confidence is further compromised. Accordingly, even if death is avoided, the injuries suffered from a fall can be devastating to the person's physical and mental well-being.

This further background as to Balance Test device and system for a Modern Functional Reach Test Kit should be useful. The Functional Reach Test (FRT) is a measure of flexibility, often used in physical and occupational therapy to measure mobility. Currently, the FRT is conducted in a specific location, usually the rehabilitation center, and is highly dependent on the operator. Part of this is to ensure the test is performed properly by approval of an expert, but also to ensure safety for patients with limited motion. Dumisani Mlungwana has created a universal portable Reach Test Kit that will ensure consistency with measurements while maintaining patient privacy and safety. He focused on stability and mobility for his design. This is because the reach test kit must be able to be moved close to the patient to conduct the test and the device should not harm the patient if it falls.

Problem Solved

The Functional Reach Test is a non-invasive measuring device used to perform a functional reach test to assess balance and functional motion to help determine if patients are ready to be released from hospital settings. The Functional Reach Test is easy to use, portable, and more consistent than the current method. These observations and areas of need are identified in the following Table.

| Category | Description of Current Methods | Need/Problem Solves |
|---|---|---|
| Portability | Current methods require the device to be set up in in specific locations, | There is a need for a portable device that will remain consistent when assembled in different places so that the device can be used in patient privacy. |
| Accessibility and usability | Instructions for the device, if any, are lacking and unclear, | Device must be easily usable for a wide variety of users and gather consistent results from user to user. |
| Easy to Clean | Currently, it is challenging to properly clean devices. | Disinfection process must be fast and simple. |

A goal was to create a device with a sturdy but lightweight structure that was portable and could accommodate all patient heights. The major design specifications that needed to be tackled were lightweight, compact, durable, and rigid. The design is under 6 pounds, has a carrying case, tested durable, and shows promise of great lifetime. It is also relatively quick and easy to manufacture allows time for user testing.

Prior Art

As far as known, there are no to Balance Test device and system for a Modern Functional Reach Test Kit device or the like. It is believed that this product is unique in its design and technologies. A novelty search revealed:

A. A Publication of US patent application US2015/0116120 named a Motion Monitoring Device applied for by Watanabe in 2015. It describes a motion monitoring device includes a detection section attached to a test subject and adapted to detect a motion of the test subject, a determination section adapted to determine whether displacement information of the test subject obtained based on a detection data from the detection section exceeds a threshold value, and an announcement section adapted to make an announcement to the test subject based on the determination.

B. A Publication of US patent application US2012/0101411 entitled Automated Near-Fall Detector was applied for by Hausdorff et al in 2012. It teaches a method of gait data collection, the method comprising collecting movement data, determining from the data a movement parameter that includes a third order derivative of position, comparing the movement parameter with a threshold value, and counting at least a near fall if the movement parameter exceeds the threshold value.

C. U.S. Pat. No. 7,972,246 named Walking Ability Diagnosis System issued by Shinomiya et al in 2011. It provides a sensor unit installed in a premises for detecting a user's walking behavior. Connected to the server through a communication network are a server, an information reporting unit, and an exercise machine. The server includes a diagnosis section for analyzing time series data of walking signal from the sensor unit to determine walking ability and generate walking ability data indicative thereof, and an information providing section which provides the walking ability date to the information reporting unit and the exercise machine. The information reporting unit includes reporting means for reporting the determined walking ability to the user. The exercise machine includes a control section which gives an exercise to the user depending upon the walking ability.

D. A Publication of US patent application US2008/0281550 titled Systems and Methods for Characterizing Balance Function and submitted by Hogle et al. It shows a systems and methods for characterizing balance function. In particular, the present invention provides systems and methods for monitoring balance function (e.g., in a single individual and/or plurality of individuals), generating one or more databases comprising balance function data, processing and/or analyzing databases comprising balance function data, and characterizing balance function (e.g., in a single individual and/or plurality of individuals (e.g., utilizing databases comprising balance function data)). Systems and methods of the present invention find use in, among other things, research, diagnostic and therapeutic applications.

E. A Publication of US patent application US2006/0251334 called a Balance Function Diagnostic System and Method was applied for by Oba et al. It teaches a balance diagnostic apparatus and system is given a portable size and weight and expands the places of use and methods of use to a large range, thus achieving an environment where anyone can undergo diagnosis of balance disorders at any time or any place. At least motion sensor means 10 and motion storage means that temporarily stores signals that represent motion from the motion sensor means are worn on the body of the user. Moreover, once the motion situation is stored in the motion storage means, the input of the motion diagnosis means is connected to the output of the motion storage means to obtain the output of diagnostic results with this balance function diagnostic system.

F. Publication of US patent application US2006/0073941 was entitled Proprioception Machine and submitted by Perry et al. It is a proactive machine is used for assessing and improving a user's proprioception. The machine has a tilting platform upon which the user stands, a non-rotating tilting means connected to the platform for tilting the platform along a first axis and along a second axis perpendicular to the first axis, and a control means for controlling the tilting means.

As can be observed, none of the prior art has anticipated or caused one skilled in the art of physical tests for balance and reach devices to see this new invention by the Mlungwana as obvious to a person skilled in the ordinary art of the industry. The Balance Test device and system for a Modern Functional Reach Test Kit provides an answer needed for Portability, Accessibility, and usability, and Easy to Clean.

SUMMARY OF THE INVENTION

The Functional Reach Test Kit is a non-invasive measuring device used to perform a functional reach test to assess balance and functional motion to help determine if patients are ready to be released from hospital settings. The Functional Reach Test Kit is easy to use, portable, and more consistent than the current method. It is intended to use at the practitioner's discretion for the quantification of balance and mobility by providing a comprehensive system that produces reliable measurements considering posture and orientation while preventing overextension. The modernized functional reach test kit is easily moved to a variety of locations, functional at a variety of locations to maintain the privacy of the patient, easy to clean, and comes with a clear set of instructions for ease of use.

The preferred embodiment of the balance Test device for a modern Functional Reach Test (FRT) comprised of: (a) a tripod Leg assembly; (b) a sectioned, vertical laser pole; (c) a horizontal bar; (d) A means to connect the vertical laser pole to the horizontal bar; (e) a means to connect the vertical laser pole to the tripod leg assembly; and (f) a Target Slider and digital calibrator measurer wherein the Functional Reach Test is lightweight, compact, durable, and rigid and provides a non-invasive measuring device used to perform a functional reach test to assess balance and functional motion to help determine if patients are ready to be released from hospital settings.

The newly invented Balance Test device and system for a Modern Functional Reach Test Kit can be manufactured at low volumes by very simple means and in high volume production by more complex and controlled systems.

Objects and Advantages

There are several objects and advantages of the Balance Test device and system for a Modern Functional Reach Test Kit. There are currently no known balance and reach tests that are effective at providing the objects of this invention.

Balance Test device and system for a Modern Functional Reach Test Kit has the following various advantages and benefits:

| Item | Customer Requirements | Rationale |
| --- | --- | --- |
| 1 | Strong, rigid material | The device must be able to withstand impact in a situation of loss of balance. |
| 2 | Able to fit into carrying case | The device must be easily packed and moved to various locations. |
| 3 | Reproducible | Consistency is key to providing reliable data and useful measurements. |
| 4 | Repeatable | The device must produce reliable data in various settings. |
| 5 | No rough edges | The device must be comfortable and safe for patient use. |
| 6 | Lightweight | The device must be easy to move to various locations. |
| 7 | Able to be used on various surfaces | The device must produce reliable data in various settings. |
| 8 | Usable | The device should be easy to assemble and use for patients and clinicians. |

Finally, other advantages and additional features of the present Balance Test device and system for a Modern Functional Reach Test Kit will be more apparent from the accompanying drawings and from the full description of the device. For one skilled in the art of balance and reach tests, it is readily understood that the features shown in the examples with this product are readily adapted to other types of physical tests for balance and reach devices.

DESCRIPTION OF THE DRAWINGS—FIGURES

The accompanying drawings, which are incorporated in and constitute a part of this specification, illustrate an embodiment of the Balance Test device and system for a Modern Functional Reach Test Kit that is preferred. The drawings together with the summary description given above and a detailed description given below explain the principles of the Balance test device and system. It is understood, however, that the Balance Test device and system for a Modern Functional Reach Test Kit is not limited to only the precise arrangements and instrumentalities shown.

FIGS. 1 A through 1 C are sketches of the general Balance Test and Functional Reach Test for Physical Testing device.

FIGS. 2 A through 2 D are sketches of the general Balance Test and Functional Reach Test for Physical Testing device with several components and features noted.

FIGS. 3 A through 3 I are more sketches of the Balance Test and Functional Reach Test for Physical Testing device with the components and features shown from generally a top view.

FIGS. 4 A through 4 C are sketches of prototypes of the Balance Test and Functional Reach Test for Physical Testing device with components noted.

FIGS. 5 A through 5 D are sketches of stress parts, displacement parts and prototypes of the Balance Test and Functional Reach Test for Physical Testing device.

FIGS. 6 A through 6 D are test results of clinical trials of the Balance Test and Functional Reach Test for Physical Testing device.

FIGS. 7 A through 7 C are more test results for the clinical trials of the Balance Test and Functional Reach Test for Physical Testing device.

FIGS. 8 A through 8 E are sketches of setting up and operating the Balance Test and Functional Reach Test for Physical Testing device.

FIGS. 9 A and 9 B are sketches of instructional pamphlet for the Balance Test and Functional Reach Test for Physical Testing device.

Figure 10:
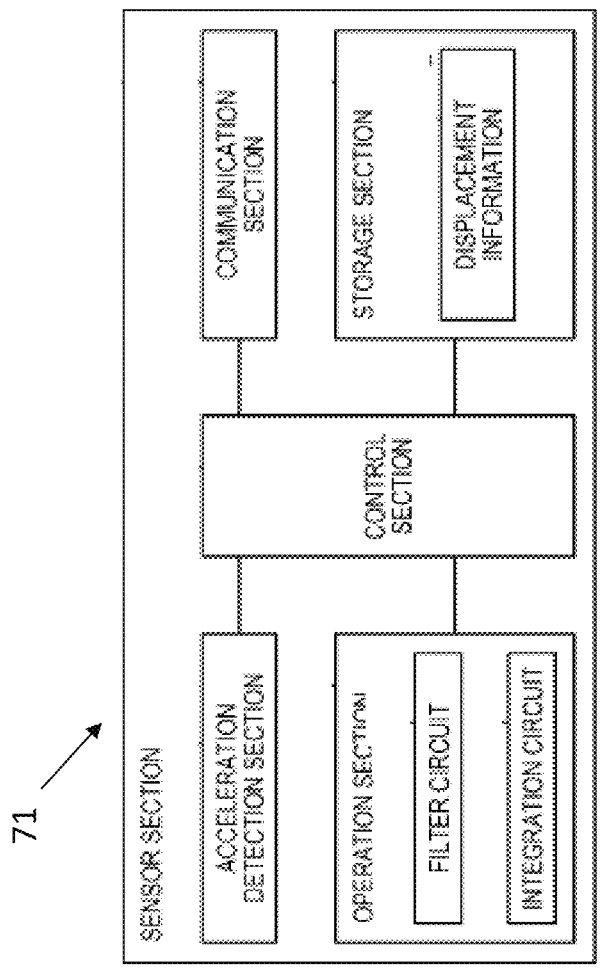
Figure 10:
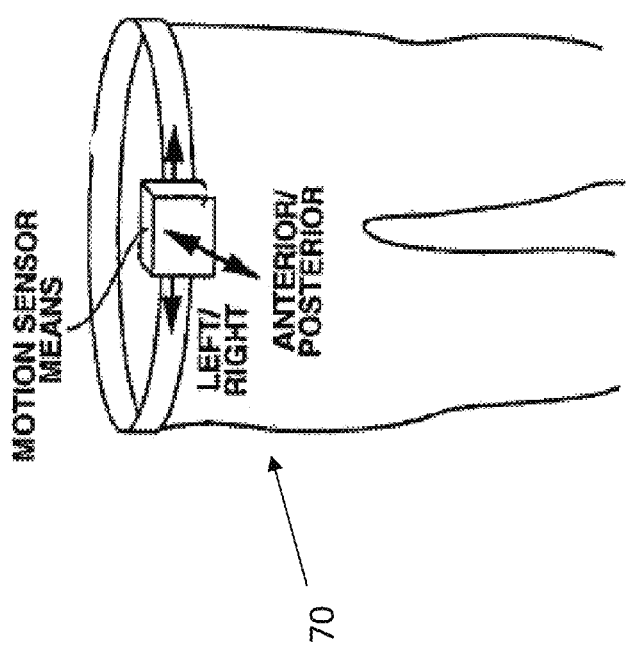
Figure 10:
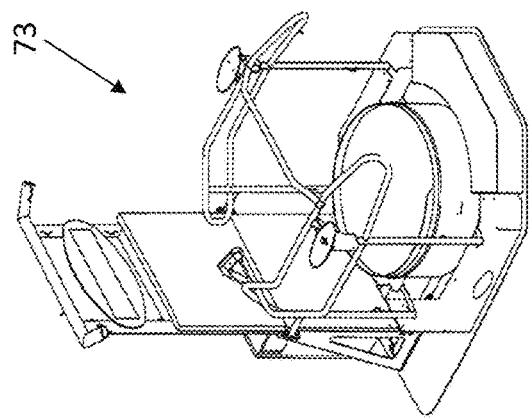
Figure 10:
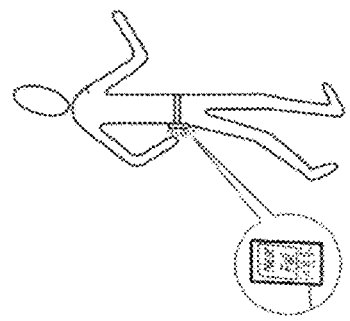
Figure 10:
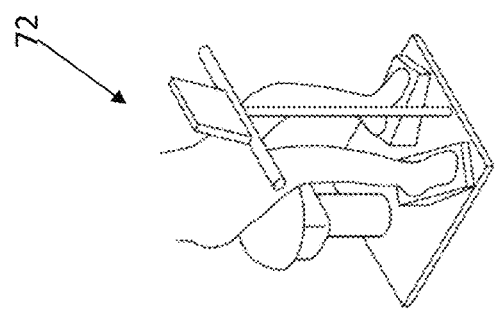

FIGS. 10 A through 10 E are sketches of prior art devices for other balance and reach tests.

DESCRIPTION OF THE DRAWINGS—REFERENCE NUMERALS

The following list refers to the drawings:

TABLE B

Reference numbers

| Ref # | Description |
| --- | --- |
| 30 | Balance Test device and system 30 for a modern Functional Reach Test (FRT) Kit. |
| 35 | Prototype 1—35 with Sturdy base 61 with locking casters 62 |
| 36 | Clamps 36 to attach to doorway |
| 37 | Clamp base 37 to attach to bed or framework |
| 38 | Tripod base Functional Reach Test Prototype 2—38 |
| 40 | Adir Pro Telescoping Laser Pole 40 or equal |
| 41 | Digital calibration/measure 41 unit |
| 45 | Aluminum Square Tube, Horizontal Bar, Square Aluminum Tubing 45 or equal—square aluminum tubing is lightweight, inexpensive, durable, and low coefficient of friction. Square tubing selected so the slider does not rotate about longitudinal axis of the horizontal bar; Everbilt 36 in. × ¾ in × 1/16 in. |
| 46 | 3D Printed PLA Target Slider 46—lightweight, and durable PLA was expensive and easy to produce. |
| 46A | Target perimeter 46A |
| 46B | Target mounting aperture 46B surrounding horizontal bar 45 |
| 46C | Initial target slider prototype 46C |
| 47 | Clamp, Vise clamp 47, inexpensive and ease of attachment to adjustable platform on the Adir pro Caidu; Vises mini-Vise Clamp |
| 48 | Sturdy base 48 with locking casters 35A |
| 51 | Tripod Leg assembly 51; Base, Survey tripod 51—already manufactured lightweight (<6 lbs., inexpensive, has an adjustable vertical platform comes with a bag that can carry the components Adir Pro Telescoping Laser Pole |
| 51A | A means 51A for connecting the tripod to the vertical laser pole 54 such as a Lock mechanism for tripod leg assembly 51 |
| 52 | A means to connect 52 the Telescoping laser pole 54 to the horizontal bar 45 such as a mounting platform |
| 53 | Adjustment knob 53 |
| 53A | Knob threaded shaft and aperture 53A to hold vise 56 |
| 53B | Lock mechanism 53B locking mounting 52 to vertical pole 54 |
| 54 | Vertical laser pole 54 with sections 54A, B, C |
| 54D | Threaded or press flat removable securing means 54D |
| 56 | Vise clamp 56 |
| 57 | PVC Pipe 57 |
| 58 | PVC Tee 58 or 4-way 58A |
| 59 | Fastener means 59 such as screws, bolts, hose clamps, or the like |
| 60 | User/therapist 60 |
| 61 | Wood base structure 61 |
| 62 | Wheels, casters 62 |
| 63 | Vertical post 63 |
| 64 | Top rail 64 |
| 65 | Clamp 65 |
| 70 | Prior art 70 publication of US patent application US2006/0251334 Balance Function Diagnostic System and Method Oba et al. |
| 71 | Prior art 71 publication of US Patent application US2015/0116120 Motion Monitoring Device by Watanabe |
| 72 | Prior art 72 of US Patent 7,972,246 Walking Ability Diagnosis System issued by Shinomiya et al. |
| 73 | Prior art 73 publication of US Patent application US2006/0073941 Proprioception Machine by Perry et al. |

TABLE B-continued

Reference numbers

| Ref # | Description |
| --- | --- |
| 74 | Prior art 74 publication of US patent application US2006/0251334 Balance Function Diagnostic System and Method Oba et al. |
| 80 | Patient 80 |
| 81 | Stress plot 81 of displacement 82 of prototype 1—35 |
| 82 | Displacement plot 82 of prototype 1—35 |
| 83 | Test reach distance 83 |
| 83A | Test user data 83A of clinical reach distance 83 |
| 84 | Repeatability by user chart 84 |
| 85 | Repeatability summary chart 85 |
| 86 | Age chart 86 of users/patient 80 |
| 87 | Reproducibility chart 87 |
| 88 | Repeatability chart 88 |
| 89 | Assembly time 89 for prototype 2—38 |
| 90 | Instructional pamphlet View A 90 instruction pamphlet view B 91 |
| 91 | Instruction pamphlet view A 90 instruction pamphlet view B 91 |
| 100 | Patient 80 using 100 the FRT 30 |

DETAILED DESCRIPTION OF PREFERRED EMBODIMENT

The present development is a Balance Test device and system for a Modern Functional Reach Test Kit. The present invention relates to systems and methods for characterizing balance function. In particular, the present invention provides systems and methods for monitoring balance function. Systems and methods of the present invention find use in, among other things, research, diagnostic and therapeutic applications. The present invention, in some embodiments thereof, relates to motion detection, and more particularly, but not exclusively, to a system useful for identifying balance and reach related to motion.

The advantages for the Balance Test device and system 30 for a Modern Functional Reach Test are listed above in the introduction. Succinctly the benefits are that the device:

A. Strong, rigid material—The device must be able to withstand impact in a situation of loss of balance.
B. Able to fit into carrying case—The device must be easily packed and moved to various locations.
C. Reproducible—Consistency is key to providing reliable data and useful measurements.
D. Repeatable—The device must produce reliable data in various settings.
E. No rough edges—The device must be comfortable and safe for patient use.
F. Lightweight—The device must be easy to move to various locations.
G. Able to be used on various surfaces—The device must produce reliable data in various settings.
H. Usable—The device should be easy to assemble and use for patients and clinicians.

The preferred embodiment of the balance Test device 30 for a modern Functional Reach Test (FRT) comprised of: (a) a tripod Leg assembly 51; (b) a sectioned, vertical laser pole 54; (c) a horizontal bar 45; (d) A means to connect 52 the vertical laser pole 54 to the horizontal bar 45; (e) a means to connect 51A the vertical laser pole 54 to the tripod leg assembly 51; and (f) a Target Slider 46 and digital calibrator measurer 41 wherein the Functional Reach Test is lightweight, compact, durable, and rigid and provides a non-invasive measuring device used to perform a functional reach test to assess balance and functional motion to help determine if patients are ready to be released from hospital settings.

There is shown in FIGS. 1-10 a complete description and operative embodiment of the Balance Test device and system 30 for a Modern Functional Reach Test Kit. In the drawings and illustrations, one notes well that the FIGS. 1-10 demonstrate the general configuration and use of this product. The various example uses are in the operation and use section, below. The accompanying drawings, which are incorporated in and constitute a part of this specification, illustrate a Balance Test device and system 30 that is preferred. The drawings together with the summary description given above and a detailed description given below explain the principles of the device and system. It is understood, however, that the Balance Test device and system 30 for a Modern Functional Reach Test Kit is not limited to only the precise arrangements and instrumentalities shown. Other examples are still understood by one skilled in the art of functional reach and balance tests and associated equipment to be within the scope and spirit shown here.

Figure 1A:
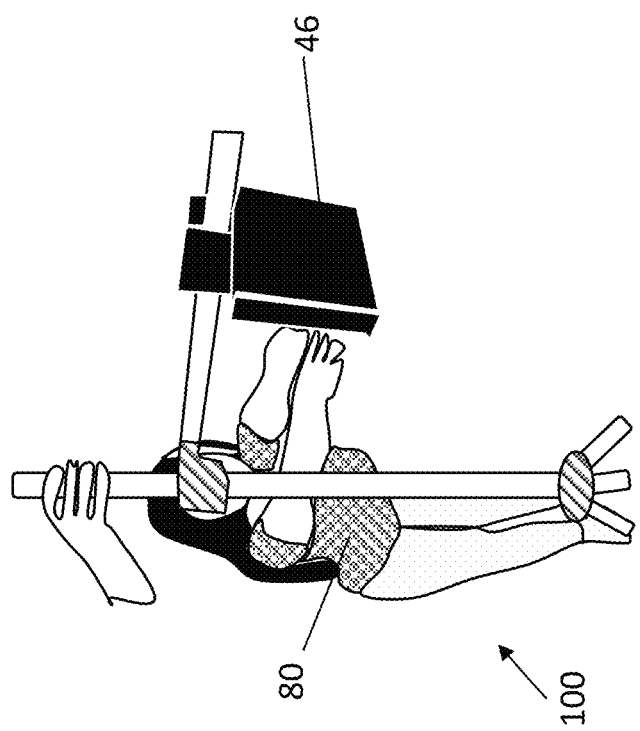
Figure 1B:
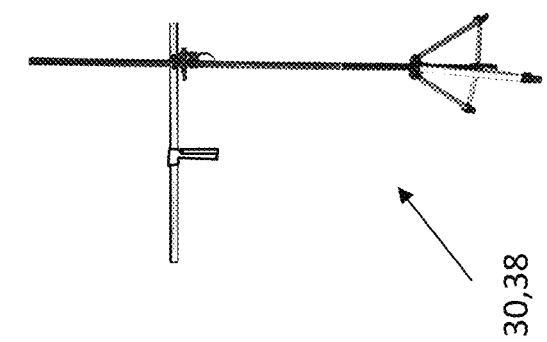
Figure 1C:
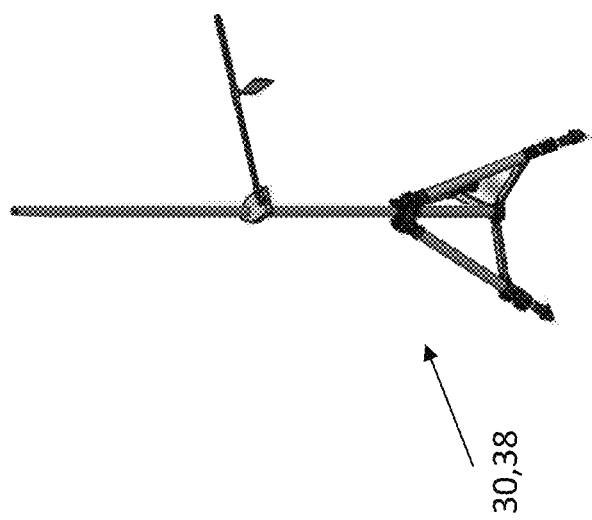

FIGS. 1A through 1C are sketches of the general Balance Test and Functional Reach Test 30 for Physical Testing device. Provided in these summary sketches are a balance Test device and system 30 for a modern Functional Reach Test (FRT) Kit; a tripod base Functional Reach Test Prototype 2—38; a 3D Printed PLA Target Slider 46—lightweight, and durable PLA was expensive and easy to produce; a patient 80; and a patient 80 using 100 the FRT 30. One notes that the design features a tripod with an adjustable platform for vertical calibration and a level to ensure measurements are taken on a flat surface, a lightweight sliding target, a horizontal bar with visible ruler tape for simple measurements, and a carrying case for all of the materials to be transported.

FIGS. 2A through 2D are sketches of the general Balance Test and Functional Reach Test for Physical Testing device 30 with several components and features noted. Demonstrated here are a balance Test device and system 30 for a modern Functional Reach Test (FRT) Kit; a tripod base Functional Reach Test Prototype 2—38; a digital calibration/measure 41 unit; an aluminum Square Tube, Horizontal Bar, Square Aluminum Tubing 45 or equal—square aluminum tubing is lightweight, inexpensive, durable, and low coefficient of friction. Square tubing selected so the slider doesn't rotate about longitudinal axis of the horizontal bar; Everbilt 36 in.×¾ in×¹⁄₁₆ in.; a 3D Printed PLA Target Slider 46—lightweight, and durable PLA was expensive and easy to produce; a target perimeter 46A; a target mounting aperture 46B surrounding horizontal bar 45; a tripod Leg assembly 51; Base, Survey tripod 51—already manufactured lightweight (<6 lbs., inexpensive, has an adjustable vertical platform comes with a bag that can carry the components Adir Pro Telescoping Laser Pole; a means 51A for connecting the tripod to the vertical laser pole 54 such as a Lock mechanism for tripod leg assembly 51; a means to connect 52 the Telescoping laser pole 54 to the horizontal bar 45 such as a mounting platform; a vertical laser pole 54; and a set of laser pole sections 54A,B,C. One can observe that the finalized design features a tripod with an adjustable platform for vertical calibration and a level to ensure measurements are taken on a flat surface, a lightweight sliding target, a horizontal bar with visible ruler tape for simple measurements, and a carrying case for all of the materials to be transported. The tripod base of the device is ensured to be mechanically sound and stable according to Adir Pro and easily handles the additional weight of the horizontal calibrator, clamp, and slider. It is also versatile with adjustable legs and adjustable heights that can be customized for each patient. The administered FRT does not add any load to the tripod but it can hold 200 plus pounds and is durable enough for more than the drop test. The vise clamp offers enough support for the horizontal calibrator but fails to bear ten (10) pounds more on the extended part keeping the test valid by not allowing any weight displacement and provides safety by not letting the tripod tip over. The slider works with a small enough coefficient of friction where it slides but cannot be pushed or thrown farther than the patient can reach.

FIGS. 3 A through 3 I are more sketches of the Balance Test and Functional Reach Test for Physical Testing device with the components and features shown from generally a top view. Components and features shown here include: a balance Test device and system 30 for a modern Functional Reach Test (FRT) Kit; a tripod base Functional Reach Test Prototype 2—38; an aluminum Square Tube, Horizontal Bar, Square Aluminum Tubing 45 or equal—square aluminum tubing is lightweight, inexpensive, durable, and low coefficient of friction. Square tubing selected so the slider doesn't rotate about longitudinal axis of the horizontal bar; Everbilt 36 in.×¾ in×¹⁄₁₆ in.; a 3D Printed PLA Target Slider 46—lightweight, and durable PLA was expensive and easy to produce; a target perimeter 46A; a target mounting aperture 46B surrounding horizontal bar 45; a tripod Leg assembly 51; Base, Survey tripod 51—already manufactured lightweight (<6 lbs., inexpensive, has an adjustable vertical platform comes with a bag that can carry the components Adir Pro Telescoping Laser Pole; a means 51A for connecting the tripod to the vertical laser pole 54 such as a Lock mechanism for tripod leg assembly 51; a means to connect 52 the Telescoping laser pole 54 to the horizontal bar 45 such as a mounting platform; an adjustment knob 53; a knob threaded shaft and aperture 53A to hold vise 56; a lock mechanism 53B locking mounting 52 to pole 54; a vertical laser pole 54 with sections 54A,B,C; a set of laser pole sections 54A,B,C; a threaded or press flat removable securing means 54D; and a vise clamp 56. Again, the finalized design features a tripod with an adjustable platform for vertical calibration and a level to ensure measurements are taken on a flat surface, a lightweight sliding target, a horizontal bar with visible ruler tape for simple measurements, and a carrying case for all of the materials to be transported.

FIGS. 4 A through 4 C are sketches of prototypes of the Balance Test and Functional Reach Test for Physical Testing device 30 with components noted. Demonstrated are a balance Test device and system 30 for a modern Functional Reach Test (FRT) Kit; a prototype 1—35 with Sturdy base 61 with locking casters 62; a clamp(s) 36 to attach to doorway; a clamp base 37 to attach to bed or framework; an aluminum Square Tube, Horizontal Bar, Square Aluminum Tubing 45 or equal—square aluminum tubing is lightweight, inexpensive, durable, and low coefficient of friction. Square tubing selected so the slider does not rotate about longitudinal axis of the horizontal bar; Everbilt 36 in.×¾ in×¹⁄₁₆ in.; a 3D Printed PLA Target Slider 46—lightweight, and durable PLA was expensive and easy to produce; a means to connect 52 the Telescoping laser pole 54 to the horizontal bar 45 such as a mounting platform; a vertical laser pole 54; a wood base structure 61; a set of swivel or lockable wheels, casters 62; a vertical post 63; a top rail 64; and a clamp 65. These FIG. 4 A shows: A Sturdy base with locking casters. Design is portable and able to be moved directly to a patient. Base design is heavy and does not allow for additional patient support. FIG. 4 B shows: Clamps to attach to a doorway. Utilizing the doorway for stability will decrease the overall weight of the device and allow for additional patient stability mechanisms. Design can only be used in a doorway and involves the patient reaching through which may obstruct the area. And FIG. 4C shows: Clamp at base to attach to bed frame or other study frame. Using a clamp for stability will decrease the weight of the device and increase portability. Design could be less stable and relies on the clamping beam. If the clamping beam fails, the Device could cause an adverse event.

FIGS. 5 A through 5 D are sketches of stress parts, displacement parts and prototypes of the Balance Test and Functional Reach Test for Physical Testing device 30. Shown in these sketches are a balance Test device and system 30 for a modern Functional Reach Test (FRT) Kit; a prototype 1—35 with Sturdy base 61 with locking casters 62; a tripod base Functional Reach Test Prototype 2—38; an aluminum Square Tube, Horizontal Bar, Square Aluminum Tubing 45 or equal—square aluminum tubing is lightweight, inexpensive, durable, and low coefficient of friction. Square tubing selected so the slider does not rotate about longitudinal axis of the horizontal bar; Everbilt 36 in.×¾ in×¹⁄₁₆ in.; a 3D Printed PLA Target Slider 46—lightweight, and durable PLA was expensive and easy to produce; an initial target slider prototype 46C; a length of PVC Pipe 57; a PVC 3-way Tee 58 or 4-way Tee 58A; a fastener means 59 such as screws, bolts, hose clamps, or the like; a wood base structure 61; a set of swivel or lockable wheels, casters 62; a stress plot 81 of displacement 82 of prototype 1—35; and a displacement plot 82 of prototype 1—35.

| Item Description | Purpose |
| --- | --- |
| 1.5 × 10 ft PVC—Genova Products | Prototype body |
| Screws | Fastening Prototype |
| Fixed Bolted 90 Degree | Calibration |
| Dual Clamp | Vertical Adjustability |
| PVC Charlotte Pipe Tee | Target support Horizontal testing |
| Galvanized steel Angle | Structural Support |
| 2 × 4 × 96 Premium Stud | Base Construction |

In the design process of the prototype, it was understood that the design needed to be able to support or catch the patient in the situation of loss of balance or falling. Later it became clear it was not necessary to catch the patient if they fell. It was then determined that the design would move forward with the features a free-standing device that is able to be wheeled around to various locations. Prototype I showed good statistical results supporting repeatability and reproducibility but had obvious design issues. The two most outstanding issues were that the slider rotated too easily around the horizontal calibrator and had to be held in place by the proctor and that the prototype didn't accomplish the goal of mobility with a weight above 20 pounds and volume above 0.05 cubic meters. Shown in FIG. 5 D is the second prototype and final design. Utilizing the results from the user testing done with Prototype I, it was determined that because the sliding mechanism yielded accurate results, a similar method could be used in the next iteration of the device. The horizontal rod was changed from circular PVC to square aluminum tubing to eliminate the rotation of the target. A telescoping structure was designed but ultimately, the Adir Pro laser tripod mount was purchased instead of manufacturing the telescoping base to allow for adequate time to conduct user testing. A vise was attached to the platform that came with the tripod mount and a target was 3D printed with PLA. After the completion of manufacturing, Prototype II was utilized for user testing.

FIGS. 6 A through 6 D are test results of clinical trials of the Balance Test and Functional Reach Test for Physical Testing device. FIGS. 7 A through 7 C are more test results for the clinical trials of the Balance Test and Functional Reach Test for Physical Testing device. FIGS. 8 A through 8 E are sketches of setting up and operating the Balance Test and Functional Reach Test for Physical Testing device. FIGS. 9 A and 9 B are sketches of instructional pamphlet for the Balance Test and Functional Reach Test for Physical Testing device. These are related to the operation of the device and system and are described below in the operations section.

FIGS. 10 A through 10 E are sketches of prior art devices for other balance and reach tests. Here former patents and applications for various devices and systems are shown. They include: Prior art 70 publication of US patent application US2006/0251334 Balance Function Diagnostic System and Method Oba et al.; Prior art 71 publication of US Patent application US2015/0116120 Motion Monitoring Device by Watanabe; Prior art 72 of U.S. Pat. No. 7,972,246 Walking Ability Diagnosis System issued by Shinomiya et al.; Prior art 73 publication of US Patent application US2006/0073941 Proprioception Machine by Perry et al.; and Prior art 74 publication of US patent application US2006/0251334 Balance Function Diagnostic System ad Method Oba et al. As can be seen, in comparison, the Balance Test device and system for a Modern Functional Reach Test Kit is a unique combination and use as described herein.

The anticipated durable materials for balance Test device 30 for a modern Functional Reach Test (FRT) include: For the tripod assembly 51—metals such as aluminum, steel, steel alloy, stainless steel, galvanized steel, brass, and the like and polymers—urethane, nylon, reinforced nylon, polyvinyl chloride (PVC), silicone, Pebax® Elastomers—A family of lightweight polymers, thermoplastic elastomers (TPE) or other composite material. For the rigid sectioned, vertical laser pole 54 or the horizontal bar 45: metals such as aluminum, steel, steel alloy, stainless steel, galvanized steel, brass, and the like and polymers—urethane, nylon, reinforced nylon, polyvinyl chloride (PVC), silicone, Pebax® Elastomers—A family of lightweight polymers, thermoplastic elastomers (TPE) or other composite material; And for the Target Slider 46 and digital calibrator measurer 41 metals such as aluminum, steel, steel alloy, stainless steel, brass, and the like and polymers—urethane, nylon, reinforced nylon, polyvinyl chloride (PVC), Acrylonitrile butadiene styrene (ABS), silicone, thermoplastic elastomers (TPE) or other composite material. Recall that the aluminum Square Tube, Horizontal Bar, Square Aluminum Tubing 45 or equal—square aluminum tubing is lightweight, inexpensive, durable, and low coefficient of friction aluminum Square Tube, Horizontal Bar, Square Aluminum Tubing 45 or equal square tubing; the fastener means 59 are such as screws, bolts, hose clamps, or the like, and the rollers are a set of swivel or lockable wheels or casters 62.

The details mentioned here are exemplary and not limiting. Other specific components and manners specific to describing a Balance Test device and system for a Modern Functional Reach Test Kit can be added by a person having ordinary skill in the field of the art of testing and observation devices and systems for balance and reach.

OPERATION OF THE PREFERRED EMBODIMENT

The Balance Test device and system 30 for a Modern Functional Reach Test Kit has been described in the above embodiment. The manner of how the device operates is described below. One notes well that the description above and the operation described here must be taken together to fully illustrate the concept of the balance and reach device and system. The preferred embodiment of the balance Test device 30 for a modern Functional Reach Test (FRT) comprised of: (a) a tripod Leg assembly 51; (b) a sectioned, vertical laser pole 54; (c) a horizontal bar 45; (d) A means to connect 52 the vertical laser pole 54 to the horizontal bar 45; (e) a means to connect 51A the vertical laser pole 54 to the tripod leg assembly 51; and (f) a Target Slider 46 and digital calibrator measurer 41 wherein the Functional Reach Test is lightweight, compact, durable, and rigid and provides a non-invasive measuring device used to perform a functional reach test to assess balance and functional motion to help determine if patients are ready to be released from hospital settings.

FIGS. 8 A through 8 E are sketches of setting up and operating the Balance Test and Functional Reach Test for Physical Testing device. Shown are a balance Test device and system 30 for a modern Functional Reach Test (FRT) Kit; a tripod base Functional Reach Test Prototype 2—38; a digital calibration/measure 41 unit; an aluminum Square Tube, Horizontal Bar, Square Aluminum Tubing 45 or equal—square aluminum tubing is lightweight, inexpensive, durable, and low coefficient of friction. Square tubing selected so the slider doesn't rotate about longitudinal axis of the horizontal bar; Everbilt 36 in.×¾ in×¹⁄₁₆ in.; a 3D Printed PLA Target Slider 46—lightweight, and durable PLA was expensive and easy to produce; a target perimeter 46A; a target mounting aperture 46B surrounding horizontal bar 45; a tripod Leg assembly 51; Base, Survey tripod 51—already manufactured lightweight (<6 lbs., inexpensive, has an adjustable vertical platform comes with a bag that can carry the components Adir Pro Telescoping Laser Pole; a means 51A for connecting the tripod to the vertical laser pole 54 such as a Lock mechanism for tripod leg assembly 51; a laser pole 54; a set of laser pole sections 54A,B,C; a threaded or press flat removable securing means 54D; an user/therapist 60; a patient 80; and a clinical reach distance 83.

Manufacturing Process for the balance Test device and system 30 for a modern Functional Reach Test (FRT) Kit is:
  A. Assembly Instructions (Set Up)
    Take out all parts from bag:
      1. Tripod 51
      2. Platform mounting 52
      3. Rods (numbered 1-3) 54 (tripod) and 54A, B and C
      4. Target 46
      5. Aluminum horizontal arm 45
  B. Assembly Instructions (Tripod)
    1. Open tripod 51
    2. Place rod (1) 54C in center rod 54 of tripod 51
    3. Screw rod (2) 54B into rod (1) 54C
    4. Screw rod (3) 54A into rod (2) 54B
    5. Open clamp 56,53B on platform mounting 52
    6. Slide platform mounting 52 over top of device (rod 3—54A)
    7. Close platform clamp 53B at desired height C. Assembly Instructions (Slider Bar Attachment)
1. Lay end of tube flat horizontal arm 45 on platform mounting 52 and vise 56
2. Clamp horizontal flat arm 45 at one end using vise 56
3. Slide the target 46 and aperture 46B on the opposite free end of horizontal flat arm 45.

FIGS. 9 A and 9 B are sketches of instructional pamphlet for the Balance Test and Functional Reach Test for Physical Testing device. Note here: a balance Test device and system 30 for a modern Functional Reach Test (FRT) Kit; an instructional pamphlet View A 90 instruction pamphlet view B 91; and an instruction pamphlet view A 90 instruction pamphlet view B 91. FIG. 9 B states: Purpose: The Fundamental Reach Test is a non-invasive measuring device used to perform a functional reach test to assess balance and functional motion to help determine if patients are ready to be released from hospital settings. The Functional Reach Test Kit is easy to use, portable and more consistent than the current method. It is intended to use at the practitioner's discretion for the qualification of balance and mobility by providing a comprehensive system that produces reliable measurements taking into account posture and orientation while preventing overextension. Setting it up:
1. Layout all of the components and open up the tripod legs.
2. Insert the top of pole 1 through the bottom and top rings of the tripod and set in place with the set screw located on the top ring of the tripod.
3. Expand the tripod legs and put the device on the ground so it is in a level position.
4. Screw in pole 2 to the top of pole 1.
5. Slide the platform with the vise on top over pole 2 and back into position using the cam lever.
6. Slide the target onto the horizontal calibrator as shown in the figure to the right.
7. Attach the horizontal calibrator using the vice. Make sure the ruler side of the horizontal bar is facing towards the pole and the position where the slider will start is able to reach the zero position.

FIGS. 6 A through 6 D are test results of clinical trials of the Balance Test and Functional Reach Test for Physical Testing device. Shown in these drawings and charts are a test user data 83A of clinical reach distance 83; a repeatability by user chart 84; a repeatability summary chart 85; and an age chart 86 of users/patient 80. In FIG. 6 A is: Verification and validation was achieved by completing user testing on both prototypes. Because the device will be used to measure and quantify a patient's balance and mobility, while not mitigating their risk of falling, it was determined that mechanical testing was not needed for the device. Instead, extensive user testing was administered to measure the reproducibility and repeatability of the prototype of the product. User testing methods: The goal of user testing on Prototype I was to measure accuracy of device through repetitions and on different height settings. The focus of this testing was on reproducibility and repeatability of the measurements across three proctors and varying height settings. For this study, there were three proctors and three subjects, with each proctor taking five measurements for each subject. This prototype 35, shown in FIG. 5 A featured vertical adjustment for height differences, a sliding target, and a sturdy base. In FIG. 6 A shows: User testing of Prototype I yielded promising results with an average range of 1.83 inches and a standard error of <0.6 inches within trials, between measurements. Additionally, the average proctor variation was 0.4 inches for measurements taken at the proctor-specific baseline setting, 1.9 inches for measurements taken 2 settings below the baseline, and 1.4 inches for measurements taken 2 settings above the baseline. The data from user testing of Prototype I can be seen below in FIG. 6 A. Conclusions—The current metrics for determining risk levels in patients are as follows: <6 inches are high risk, 6-10 inches is moderate risk, and >10 inches are low risk. Although we received promising results with fairly low error levels, it was determined that the next iteration would need to ensure setting consistency to minimize measurement variation. Additionally, it was determined that expanding the breadth of the study would be an important improvement to ensure the device would be a reliable source of measurements for a wider demographic. The study breadth would be expanded to include a wider range of ages, levels of flexibility, and levels of operator. In FIG. 6 B is: Prototype II 38 details. Methods—The goal of user testing on Prototype II 38 was to test reproducibility and repeatability between proctors and between a subject's measurements. This was accomplished by administering two studies: Study A and Study B. The goal of Study A was to test reproducibility by measuring variation between proctors, aiming for <3 inches of variation. The goal of Study B was to test repeatability by measuring variation between measurements, aiming for <2 inches of variation. The details of both studies are listed in FIG. 6 B. A similar protocol was carried out for both studies. For Study A, an introduction to the project was given which included explaining the study, going through the consenting process, and gathering health information. Proctor 1 then set up the device, set up time was recorded, and 5 FRT measurements were taken with the subject. This process was repeated for Proctors 2 and 3, totaling in three device setups and takedowns, and 15 total FRT measurements. For Study B, the same introduction protocol was followed, then only 5 FRT measurements were taken with only 1 proctor. In FIG. 6 D are: Results—User testing results are categorized into reproducibility, repeatability, and assembly time results which are shown in FIG. 6 D. Reproducibility data represents the deviations between proctors; each proctor conducted 5 tests with the device, the average of the 5 tests were taken and standard deviations between the three proctors' averages were calculated. Then, minimum, maximum, and average standard deviations were recorded. Repeatability data represents the deviation between each test of the 5 that each proctor conducts. The minimum, maximum, and average standard deviations were calculated by examining the standard deviation between subjects' five measurements. Assembly time was recorded for each proctor (N=3) in Study A. Minimum, maximum, and average times are displayed in FIG. 6 D.

FIGS. 7 A through 7 C are more test results for the clinical trials of the Balance Test and Functional Reach Test 30 for Physical Testing device. Other charts included here are a reproducibility chart 87; a repeatability chart 88; and an assembly time 89 for prototype 2—38. In FIG. 7 A is: Reproducibility (Study A)—Study A determined that, regardless of proctor, the device predicted similar results for the same subject. This indicates that, when operated properly, the device will quantitatively measure a subject's balance and mobility consistently even if the proctor is not the same. Data is shown in FIG. 7 A where each subject's average from three proctor is displayed along with the standard deviation between the proctor's averages. In FIG. 7 B is: Repeatability (Study B)—Study B determined that the device could make repeatable measurements over the course of 5 tests with the same subject and proctor. As shown in the standard deviation bars in FIG. 7 B, variation does seem to increase when reach measurements are lower, which should be investigated in further studies. In FIG. 7 C is: Assembly Time—The assembly time data shows a clear decrease as proctors become more familiar with the device, which is to be expected. Conclusions—The specifications were well below the acceptance criteria as shown by FIG. 7 B. Repeatability and reproducibility data showed that the device can accurately and reliably conduct functional reach test measurements and assembly time indicates the ease of proctor set-up.

With this description it is to be understood that the Balance Test device and system 30 for a Modern Functional Reach Test Kit is not to be limited to only the disclosed embodiment of product. The features of the balance and reach device and system 30 are intended to cover various modifications and equivalent arrangements included within the spirit and scope of the description.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described above in the foregoing paragraphs.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

The present invention contemplates modifications as would occur to those skilled in the art. While the disclosure has been illustrated and described in detail in the figures and the foregoing description, the same is to be considered as illustrative and not restrictive in character, it being understood that only selected embodiments have been shown and described and that all changes, modifications and equivalents that come within the spirit of the disclosures described heretofore and or/defined by the following claims are desired to be protected.

What is claimed is:

1. A balance Test device (30) for a modern Functional Reach Test (FRT) made of durable materials and comprised of:
   (a) a tripod Leg assembly (51);
   (b) a sectioned, vertical laser pole (54);
   (c) a horizontal bar (45);
   (d) A means to connect (52) the vertical laser pole (54) to the horizontal bar (45);
   (e) a means to connect (51A) the vertical laser pole (54) to the tripod leg assembly (51); and
   (f) a digital calibrator measurer (41) slidably mounted to a target slider (46), both the digital calibrator measurer (41) and the Target Slider (46) made of a durable materials wherein the balance Test device (30) Functional Reach Test is lightweight, compact, durable, and rigid and provides a non-invasive measuring device used to perform a functional reach test to assess balance and functional motion to help determine if patients are ready to be released from hospital settings.

2. The balance Test device (30) for a modern Functional Reach Test (FRT) in claim 1 wherein the durable material for the Target Slider (46) and digital calibrator measurer (41) is selected from the group consisting of metals, polymers, and composite materials.

3. The balance Test device (30) for a modern Functional Reach Test (FRT) in claim 2 wherein the metal for the Target Slider (46) and digital calibrator measurer (41) is selected from the group consisting of aluminum, steel, steel alloy, stainless steel, galvanized steel, brass.

4. The balance Test device (30) for a modern Functional Reach Test (FRT) in claim 2 wherein the polymer for the Target Slider (46) and digital calibrator measurer (41) is selected from the group consisting of urethane, nylon, reinforced nylon, polyvinyl chloride (PVC), Acrylonitrile butadiene styrene (ABS), silicone, and thermoplastic elastomers (TPE).

5. The balance Test device and system (30) for a modern Functional Reach Test (FRT) Kit in claim 1 wherein an assembly process is comprised:
Step A. Assembly Instructions for Set Up—
   Take out all parts from bag:
   1. Tripod (51)
   2. Platform mounting (52)
   3. Rods (numbered 1-3) (54) (tripod) and (54A, B and C)
   4. Target (46)
   5. Aluminum horizontal arm (45)
Step B. Assembly Instructions for Tripod—
   1. Open tripod (51)
   2. Place rod (1) (54C) in center rod (54) of tripod (51)
   3. Screw rod (2) (54B) into rod (1) (54C)
   4. Screw rod (3) (54A) into rod (2) (54B)
   5. Open clamp (56,53B) on platform mounting (52)
   6. Slide platform mounting (52) over top of device (rod 3—(54A)
   7. Close platform clamp (53B) at desired height
Step C. Assembly Instructions for Slider Bar Attachment—
   1. Lay end of tube flat horizontal arm (45) on platform mounting (52) and vise (56)
   2. Clamp horizontal flat arm (45) at one end using vise (56)
   3. Slide the target (46) and aperture (46B) on the opposite free end of horizontal flat arm (45).

* * * * *